United States Patent [19]

Seemann

[11] 3,965,095

[45] *June 22, 1976

[54] OXINDOLE DERIVATIVES

[75] Inventor: Fritz Seemann, Basel, Switzerland

[73] Assignee: Sandoz Ltd., Basel, Switzerland

[*] Notice: The portion of the term of this patent subsequent to July 23, 1991 has been disclaimed.

[22] Filed: June 18, 1973

[21] Appl. No.: 370,764

[30] Foreign Application Priority Data
June 23, 1972  Switzerland.......................... 9522/72

[52] U.S. Cl..................... 260/240 J; 260/295.5 R; 260/325 R; 424/263; 424/274
[51] Int. Cl.² ........................................ C07D 209/34
[58] Field of Search ....... 260/240 J, 325 R, 295.5 R

[56] References Cited
UNITED STATES PATENTS 3,705,907  12/1972  Troxler ...................... 260/326.14 R
3,825,558  7/1974  Seemann........................ 260/325 R Primary Examiner—John D. Randolph
Attorney, Agent, or Firm—Gerald D. Sharkin; Robert S. Honor; Thomas O. McGovern

[57] ABSTRACT

The present invention concerns novel oxindole derivatives of the formula,

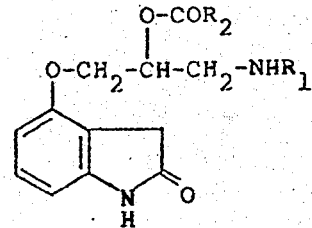

wherein $R_1$ and $R_2$ are saturated or unsaturated substituted or unsubstituted hydrocarbon radicals, useful as antiarrhythmic and $\beta$-blocking agents.

30 Claims, No Drawings

OXINDOLE DERIVATIVES

The present invention relates to oxindole derivatives. The invention provides compounds of formula I,

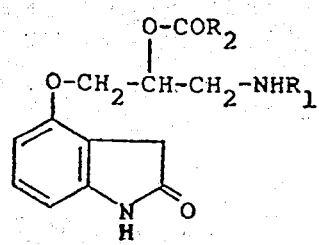

I wherein $R_1$ is (i) alkyl of 1 to 4 carbon atoms, (ii) cycloalkyl of 3 to 8 carbon atoms, (iii) phenylalkyl of 8 to 12 carbon atoms in the aggregate thereof, the phenyl ring thereof being separated from the nitrogen atom by at least two carbon atoms, (iv) phenylalkyl of 8 to 12 carbon atoms in the aggregate thereof, the phenyl ring thereof being separated from the nitrogen atom by at least two carbon atoms and being monosubstituted by alkoxy or alkyl of 1 to 4 carbon atoms, (v) alkenyl or alkinyl of 3 to 7 carbon atoms, or (vi) alkoxycarbonylalkyl, the alkyl moiety having 1 to 6 carbon atoms and the alkoxy moiety having 1 to 4 carbon atoms, and $R_2$ is (i) phenyl, (ii) phenyl monosubstituted by halogen, alkyl of 1 to 4 carbon atoms or alkoxy of 1 to 4 carbon atoms, (iii) phenylalkyl of 7 to 12 carbon atoms in the aggregate thereof or styryl, (iv) phenylalkyl of 7 to 12 carbon atoms in the aggregate thereof or styryl, monosubstituted in the phenyl ring thereof by halogen, alkyl of 1 to 4 carbon atoms or alkoxy of 1 to 4 carbon atoms, (v) a 5- or 6-membered heterocyclic ring containing a nitrogen or sulphur atom, (vi) alkoxy carbonyl alkyl, the alkyl moiety having 1 to 6 carbon atoms and the alkoxy moiety having 1 to 4 carbon atoms, (vii) adamantyl, (viii) haloalkyl of 1 to 12 carbon atoms, the halogen thereof being located in other than the α position, or, when $R_1$ is alkenyl of 3 to 7 carbon atoms (ix) alkyl of 1 to 12 carbon atoms, cycloalkyl of 3 to 6 carbon atoms, or cycloalkyl of 3 to 6 carbon atoms, mono- or poly-substituted by alkyl of 1 to 4 carbon atoms, or a 5- or 6-membered heterocyclic ring containing an oxygen atom.

When $R_1$ is alkyl, this contains preferably 3 to 5 carbon atoms. The alkyl radical is preferably branched, especially on the α carbon atom. Examples are isopropyl, sec.butyl, tert.butyl, 3-pentyl and tert.pentyl.

When $R_1$ is cycloalkyl, this contains preferably 3 to 6 carbon atoms. Examples are cyclopropyl, cyclobutyl, cyclopentyl and cyclohexyl.

When $R_1$ is phenylalkyl, this contains preferably 9 to 11 carbon atoms. The alkyl moiety thereof is preferably branched in the α position. Examples are 3-phenylpropyl, 1,1-dimethyl-3-phenylpropyl and 1,1-dimethyl-2-phenylethyl. Any alkoxy or alkyl substituent of the phenyl ring preferably contains 1 or 2 carbon atoms. Especially suited is methoxy as an alkoxy substituent, as for example in 2-(4-methoxyphenyl)-1-methylethyl, and methyl as an alkyl substituent.

When $R_1$ is alkenyl or alkinyl, this preferably contains 3 to 5 carbon atoms. The preferred substituents are branched on the α carbon atom or have the multiple bond located in other than the α position. Examples are 1,1-dimethyl-2-propionyl and allyl.

When $R_1$ is alkoxycarbonyl alkyl, the alkoxy moiety may contain especially 1 or 2 carbon atoms, and the alkyl moiety especially 3 to 5 carbon atoms. The alkyl is preferably branched on the α carbon atom. A preferred example is a 1-methyl-1-(alkoxycarbonyl)ethyl group.

When $R_2$ is or contains a phenyl group which is substituted as defined above, suitable halogen substituents are especially fluorine, chlorine or bromine, and suitable alkyl or alkoxy substituents are especially radicals containing 1 or 2 carbon atoms, e.g. methyl or methoxy.

When $R_2$ is a 5- or 6-membered heterocyclic ring, this may be saturated or unsaturated such as pyridyl, thienyl, furyl or tetrahydropyranyl.

When $R_2$ is a alkoxy carbonylalkyl the alkoxy moiety preferably is methoxy or ethoxy, and the alkyl moiety contains preferably 1 to 3 carbon atoms. Examples are alkoxycarbonylmethyl groups, e.g ethoxycarbonylmethyl.

When $R_2$ is haloalkyl, this especially signifies chloroalkyl or bromoalkyl and preferably is of 2 to 4 carbon atoms. When $R_2$ is alkyl, this especially contains 1 to 8, preferably 4 carbon atoms and may, for example, be tert.butyl. When $R_2$ is cycloalkyl substituted by alkyl of 1 to 4 carbon atoms, this is especially monoalkylated and this preferably in the 1 position of the cycloalkyl radical. An example is 1-methylcyclohexyl.

The invention provides a process for the production of a compound of formula I comprising a. acylating a compound of formula II,

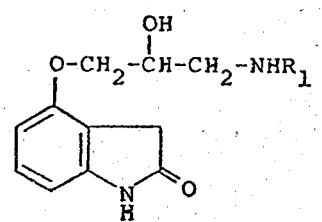

II wherein $R_1$ is as defined above, or b. debenzylating a compound of formula III,

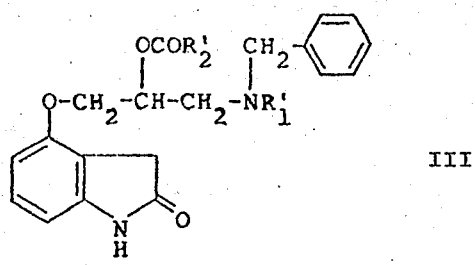

III wherein $R_1'$ is (i) alkyl of 1 to 4 carbon atoms, (ii) cycloalkyl of 3 to 8 carbon atoms, (iii) phenylalkyl of 8 to 12 carbon atoms in the aggregate thereof, the phenyl ring thereof being separated from the nitrogen atom by at least two carbon atoms, (iv) phenylalkyl of 8 to 12 carbon atoms in the aggregate thereof, the phenyl ring thereof being separated from the nitrogen atom by at least two carbon atoms and being monosubstituted by alkoxy or alkyl of 1 to 4 carbon atoms, (v) alkoxycarbonylalkyl, the alkyl moiety having 1 to 6 carbon atoms and the alkoxy moiety having 1 to 4 carbon atoms, and R$_2$' is (i) phenyl, (ii) phenyl monosubstituted by halogen, alkyl of 1 to 4 carbon atoms or alkoxy of 1 to 4 carbon atoms, (iii) phenylalkyl, or (iv) phenylalkyl monosubstituted in the phenyl ring thereof by halogen, alkyl of 1 to 4 carbon atoms or alkoxy of 1 to 4 carbon atoms, (iv) a 5- and 6-membered heterocyclic ring containing a nitrogen atom, (v) alkoxycarbonylalkyl, the alkyl moiety having 1 to 6 carbon atoms and the alkoxy moiety having from 1 to 4 carbon atoms, (vi) adamantyl, or (vii) haloalkyl of 1 to 12 carbon atoms, the halogen being located in other than the α position, to obtain a compound of formula Ia,

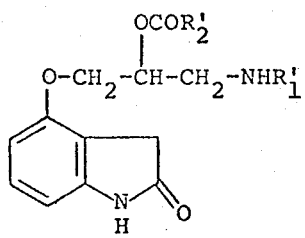

wherein R$_1$' and R$_2$' are as defined above.

For the acylation of a compound of formula II to a compound of formula I, an excess of an acid R$_2$COOH wherein R$_2$ is as defined above may be added to a compound of formula II, and an excess of the corresponding anhydride may be added to the resulting reaction mixture.

The reaction temperature may be from room temperature ot about 100°C.

The addition of R$_2$COOH may be omitted when the compounds of formula II are used in the form of a salt with a suitable mineral acid, e.g. hydrochloric acid. By protonization of the amino group of the aminopropoxy side chain the danger of an N acylation may be avoided; however, protonization is not essential, especially when R$_1$ is an α tertiary carbon atom. When the reaction is effected in the presence, for example, for hydrochloric acid, the compounds of formula I crystallize in hydrochloride form and a working up of the reaction mixture may be dispensed with. Alternatively the acylation may also be effected with an acid halide, e.g. an acid chloride in place of the anhydride. In this case the reaction is preferably effected at room temperature or at a slightly elevated temperature.

The reaction may be effected in an inert organic solvent, e.g. hexamethylphosphoric triamide, a chlorinated aliphatic hydrocarbon such as chloroform, a cyclic or open chain ether such as dioxane, or a mixture of organic solvents such as chloroform/pyridine.

The reaction mixture may be worked up, after stirring, for example, by pouring the same onto water or ice, making it alkaline with alkali carbonate or ammonia and extracting it with a water-immiscible, inert organic solvent, e.g. ethyl acetate, a cyclic or open chain ether such as diethyl ether, or a chlorinated aliphatic hydrocarbon such as methylene chloride. The working up stage should be effected carefully, to avoid splitting off of the ester group.

The debenzylation of the compounds of formula III may, for example, be effected by hydrogenation in the presence of a catalyst, preferably a palladium catalyst. The reaction may be carried out in an inert organic solvent, e.g. ethyl acetate, or a cyclic or open chain ether such as tetrahydrofuran or diethyl ether. The reaction may be preferably effected at room temperature and preferably normal pressure. After hydrogenation is complete the catalyst may be filtered off and the filtrate evaporated to dryness.

The compounds of formulae II and III are new. The compounds of formula IIa,

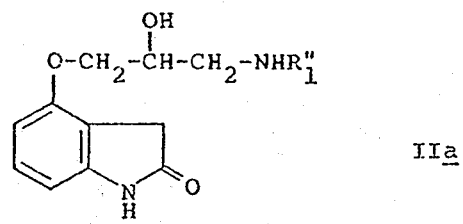

wherein R$_1$'' is alkenyl of 3 to 7 carbon atoms, are included in the present invention.

The compounds of formula II may be obtained by reacting 4-(2,3-epoxypropoxy)oxindole with an amine of formula IV,

H$_2$NR$_1$    IV wherein R$_1$ is as defined above.

The compounds of formula IIa and acid addition salt forms thereof may be obtained in accordance with the invention by reacting 4-(2,3-epoxypropoxy)oxindole with an amine of formula IVa,

H$_2$NR$_1$''    IVa wherein R$_1$'' is as defined above.

The reaction may be effected in an inert organic solvent, e.g. an aromatic hydrocarbon such as benzene, toluene or xylene, a cyclic ether such as dioxane or tetrahydrofuran, or an alcohol such as amyl alcohol.

The symbol R$_1$'' especially signifies an alkenyl group, the double bond of which is located in other than the α position and preferably contains 3 to 5 carbon atoms.

The reaction temperature may be from about 20° to 150°C. The reaction is generally preferably effected at the boiling temperature of the reaction mixture under reflux.

4-(2,3-epoxypropoxy)oxindole may, for example, be obtained by reacting the sodium salt of 4-hydroxyoxindole with epibromhydrin in dimethyl sulphoxide as solvent. After the reaction is complete the mixture may be poured in water and extracted with ethyl acetate. The ethyl acetate extracts may be concentrated until the epoxypropoxyoxindole crystallizes.

The compounds of formula III may be produced by acylating a corresponding compound of formula V,

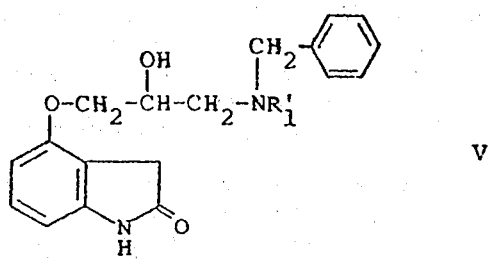

wherein $R_1'$ is as defined above,
for example, under analogous conditions to those described above for acylation of compounds of formula II.

Insofar as the production of the required starting materials is not described, these compounds are known or may be produced in accordance with known processes or in a manner analogous to the processes described herein or to known processes.

Free base forms of the compounds of formulae I and IIa may be converted into acid addition salt forms in conventional manner and vice versa.

The compounds of formula I and IIa are useful because they possess pharmacological activity in animals. In particular, the compounds are useful as agents (the compounds of formula I having prolonged action) for the prophylaxis and therapy of coronary diseases, particularly for the treatment of Angina pectoris, the hyperkinetic heart syndrome, conditions resulting from muscular hypertrophic subvalvular aortostenosis, and heart rhythm disorders, as indicated by i. an inhibition in vitro of the positive inotropic adrenalin effect in the spontaneously beating guinea pig atrium when immersed in a buffer solution containing between 0.005 and 3 mg/litre of the compound, and ii. an inhibition of the tachycardia and hypotension caused by isoproterenol [1-(3,4-dihydroxyphenyl)-2-isopropylaminoethanol] in the infusion test in the anesthetized cat and dog on administration by intravenous infusion of an effective cumulative dose of between 0.01 and 3 mg of the compound per kg animal body weight.

For the abovementioned use, the dosage administered will, of course, vary depending upon the compound employed, mode of administration and treatment desired. However, in general, satisfactory results are obtained when administered at a daily dosage of between about 0.01 and 3 mg/kg animal body weight as a single dose. The compounds may be administered as a divided dose two two to four times daily or in retard form. For compounds of formula I, this dose may be administered once daily or as a divided dose twice daily owing to their prolonged action. For larger mammals, the total daily dosage for parenteral or oral administration is in the range of from about 1 to 200 mg, and unit dosage forms suitable for parenteral or oral administration comprise from about 0.3 to 100 mg in the case of a compound of formula IIa, or from 0.3 to 200, preferably 100 to 200 mg, in the case of a compound of formula I, in a pharmaceutical composition incorporating a solid or liquid pharmaceutical carrier or diluent.

Specific examples of daily dosages, at which satisfactory results are obtained on i.v. administration, are:

i. 4-(2-benzoyloxy-3-tert-butylaminopropoxy)-oxindole, from 0.02 to 3 mg/kg animal body weight for animals in general, e.g. a dog, and for the larger mammals from 1 to 200 mg;

ii. 4-[2-(1-adamantylcarbonyloxy)-3-allylaminopropoxy]oxindole, from 0.03 to 3 mg/kg animal body weight for animals in general, e.g. a dog, and for the larger mammals from 1 to 200 mg;

iii. 4-(3-tert-butylamino-2-cinnamoyloxypropoxy)-oxindole, from 0.01 to 3 mg/kg animal body weight for animals in general, e.g. a dog, and for the larger mammals from 1 to 200 mg, and iv. 4-(3-allylamino-2-hydroxypropoxy)oxindole, from 0.2 to 3 mg/kg animal body weight for animals in general, e.g. a cat, and for the larger mammals from 1 to 200 mg.

The compounds of formula I may be administered in pharmaceutically acceptable acid addition salt form. Such acid addition salt forms exhibit the same order of activity as the free base forms and are readily prepared in conventional manner. Representative acid addition salt forms include organic acid salt forms such as the hydrogen maleate, fumarate, oxalate and methane sulphonate and mineral acid salt forms such as the hydrochloride, hydrobromide and sulphate. A pharmaceutical composition may comprise a compound of formula I, in free base form or in pharmaceutically acceptable acid addition salt form, in association with a pharmaceutical carrier or diluent. Such compositions may be prepared by conventional techniques to be in the form of, for example, capsules, tablets, suppositories, suspensions or solutions, for enteral or parenteral administration. Aside from the usual pharmaceutical diluents or carriers, e.g. water, alcohols, natural or hardened oils and waxes, these pharmaceutical compositions may contain suitable preserving, stabilizing, wetting, solubilizing, sweetening, flavouring or colouring agents.

The compounds of formula I wherein the radical $R_1$ is branched in the $\alpha$ position exhibit particularly intersecting properties.

Especially intersecting compounds of formula I are those wherein $R_2$ is phenyl, phenyl substituted by fluorine, chlorine, bromine, methoxy or methyl, or thienyl, e.g. 2-benzoyloxy-3-tert.butylaminopropoxy)oxindole and 4-[3-tert.butyl-amino-2-(2-thenoxyloxy)propoxy]oxindole.

In the following non-limitative Examples all temperatures are indicated in degrees Centigrade and are uncorrected.

EXAMPLE 1:
4-(3-allylamino-2-hydroxypropoxy)oxindole
[compound of formula IIa]

3 g of 4-(2,3-epoxypropoxy)oxindole, 30 cc of allylamine and 70 cc of dioxane are heated to the boil for 16 hours. The mixture is evaporated to dryness at reduced pressure and the crude title compound is recrystallized from ethanol/ethyl acetate. M.P. 124°–127°.

EXAMPLE 2:
4-[2-(1-adamantylcarbonyloxy)-3-allylaminopropoxy]oxindole [process variant a)]

1.35 g of 4-(3-allylamino-2-hydroxypropoxy)oxindole are converted into the hydrochloride, are then dissolved in 15 cc of hexamethyl-phosphoric acid triamide and allowed to stand at room temperature for 70 hours with 1.45 g of adamantane-1-carboxylic acid chloride. The mixture is poured into water, is rendered alkaline with a 10% ammonia solution and is extracted with methylene chloride. The evaporation residue of the methylene chloride phase is chromatographed on silica gel with methylene chloride and 1% of methanol, and the resulting title compound is converted into its hydrogen oxalate. M.P. 170°–172° from ethanol.

EXAMPLE 3:
4-(3-tert-butylamino-2-nicotinoyloxypropoxy)oxindole 1 g of 4-(3-tert-butylamino-2-hydroxypropoxy)oxindole, 20 cc of chloroform, 10 cc of pyridine and 0.713 g of nicotinoyl chloride are allowed to stand at room temperature for 4 days, the mixture is then concentrated by evaporation as carefully as possible at reduced pressure and the residue is taken up in water. The reaction mixture is rendered alkaline with a 10% ammonia solution, is extracted with methylene chloride, and subsequently an excess of 2 N hydrochloric acid in ethanol is added. The solvent and excess hydrochloric acid are carefully removed by evaporation at reduced pressure and the dihydrochloride of the title compound is crystallized from ethanol, needle druses. M.P. 215°–218°.

EXAMPLE 4:
4-[tert-butylamino-2-(2-thenoyloxy)propoxy]oxindole

The title compound is obtained in a manner analogous to that described in Example 3, using -thiophene-2-carboxylic acid chloride; the hydrogen oxalate of the title compound crystallizes from ethanol. M.P. 210°–212°.

EXAMPLE 5:
4-(3-tert-butylamino-2-cinnamoyloxypropoxy)oxindole

The title compound is obtained in a manner analogous to that described in Example 3, using cinnamic acid chloride; the hydrogen oxalate of the title compound crystallizes from ethanol in druses. M.P. 128°–132°.

EXAMPLE 6:
4-(2-benzoyloxy-3-tert-butylaminopropoxy)oxindole [process variant a)]

1 g of 4-(3-tert-butylamino-2-hydroxypropoxy)oxindole is dissolved in 20 cc of hexamethylphosphoric acid triamide and the solution is allowed to stand at room temperature for 16 hours together with 7.9 g of benzoic acid and 0.9 g of benzoic acid anhydride. The mixture is poured into ice water, is rendered alkaline with a 10% ammonia solution and is extracted with methylene chloride. The title compound is obtained as evaporation residue of the methylene chloride phase; the hydrogen oxalate of the title compound crystallizes from ethanol. M.P. 200°–203°.

EXAMPLE 7: Malonic acid ethyl-[3-tert-butylamino-1-(2-oxo-4-indolyloxy)-propyl]ester The title compound is obtained in a manner analogous to that described in Example 2 with monoethyl ester malonic acid chloride. The product which has been chromatographed several times is dissolved in absolute ether and the hydrochloride is precipitated as amorphous powder by passing dry hydrochloric acid gas through the solution.

EXAMPLE 8:
4-(3-tert-butylamino-2-phenylacetoxypropoxy)oxindole

The title compound is obtained in a manner analogous to that described in Example 3 with phenylacetic acid chloride; the hydrogen oxalate of the title compound crystallizes from ethanol in druses. M.P. 112°–115°.

EXAMPLE 9:
4-[3-tert-butylamino-2-(4-chlorobutyryloxy)propoxy]

The title compound is obtained in a manner analogous to that described in Example 6 with 4-chlorobutyric acid anhydride, except that chloroform is used as solvent in place of hexamethyl-phosphoric acid triamide. The hydrochloride of the title compound crystallizes from ethanol in prism druses having a M.P. of 171°–173°.

EXAMPLE 10:
4-(3-tert-butylamino-2-nicotinoyloxypropoxy)oxindole [process variant b)]

5 g of 4-[3-(N-benzyl-tert-butylamino)-2-nicotinoyloxypropoxy]oxindole are debenzylated with hydrogen in 25 cc of tetrahydrofuran, in the presence of 1 g of a palladium catalyst (10% of palladium on charcoal). The title compound is obtained, the dihydrochloride thereof having a M.P. of 215°–218°.

EXAMPLE 11:
4-(2-benzoyloxy-3-tert-butylaminopropoxy)oxindole

The process is effected as described in Example 10 and the title compound is obtained by debenzylation of 4-[2-benzoyloxy-3-(N-benzyl-tert-butylamino)propoxy]oxindole. The hydrogen oxalate of the title compound has a M.P. of 200°–203°.

EXAMPLE 12: Malonic acid ethyl-[3-tert-butylamino-1-(2-oxo-4-incolyloxy)-propyl]ester The process is effected as described in Example 10 and the title compound is obtained by debenzylation of malonic acid ethyl-[3-(N-benzyl-tert-butylamino)-1-(2-oxo-4-indolyloxy)propyl]ester. The hydrochloride of the title compound crystallizes from ether as amorphous powder.

EXAMPLE 13:
4-(3-tert-butylamino-2-phenylacetoxypropoxy)oxindole

The process is effected as described in Example 10 and the title compound is obtained by debenzylation of 4-[3-(N-benzyl-tert-butylamino)-2-phenylacetoxypropoxy]oxindole. The hydrogen oxalate of the title compound crystallizes from ethanol in druses. M.P. 112°–115°.

EXAMPLE 14:
4-[3-tert-butylamino-2-(4-chlorobutyryloxy)propoxy]oxindole

The process is effected as described in Example 10 and the title compound is obtained by debenzylation of 4-[3-(N-benzyl-tert-butylamino)-2-(4-chlorobutyryloxy)propoxy]oxindole. The hydrochloride of the title compound has a M.P. of 171°–173°.

The following compound is obtained in a manner analogous to that described in Example 1:
4-[2-hydroxy-3-(2-methyl-3-buten-2-ylamino)propoxy]oxindole.

The following compounds are obtained in a manner analogous to that described in Example 2:
4-[2-(2-chlorobenzoyloxy)-3-(2-methyl-3-butin-2-ylamino)propoxy]oxindole
4-[2-(4-methylbenzoyloxy)-3-(2-methyl-4-phenyl-2-butylamino)propoxy]oxindole 2-methyl-2-[2-(3-methoxybenzoyloxy)-3-(2-oxo-4-indolyloxy)propylamino]propionic acid ethyl ester
4-[3-cyclohexylamino-2-(2-thenoyloxy)propoxy]oxindole
4-(3-allylamino-2-pivaloyloxypropoxy)oxindole
4-[3-allylamino-2-(1-methylcyclohexylcarbonyloxy)-propoxy]oxindole
4-{3-[2-(4-methoxyphenyl)ethylamino]-2-pivaloyloxypropoxy}oxindole
4-[3-(2-methyl-3-buten-2-ylamino)-2-(4-tetrahydropyranylcarbonyloxy)propoxy]oxindole
4-(2-benzoyloxy-3-isopropylaminopropoxy)oxindole
4-[3-(3-pentylamino)-2-(2-thenoyloxy)propoxy]oxindole.

The following compounds are obtained in a manner analogous to that described in Example 10:
4-[2-(4-methylbenzoyloxy)-3-(2-methyl-4-phenyl-2-butylamino)propoxy]oxindole
2-methyl-2-[2-(3-methoxybenzoyloxy)-3-(2-oxo-4-indolyloxy)propylamino]propionic acid ethyl ester
4-{3-[2-(4-methoxyphenyl)ethylamino]-2-pivaloyloxypropoxy}oxindole
4-(2-benzoyloxy-3-isopropylaminopropoxy)oxindole.

Using the process exemplified in Example 2 and the appropriate starting materials, there are obtained:
4-{3-[2-(p-tolyl)ethylamino]-2-pivaloyloxypropoxy}oxindole
4-[3-allylamino-2-(p-chlorocinnanoyloxy)propoxy]oxindole
4-[3-allylamino-2-(p-methoxycinnanoyloxy)propoxy]oxindole
4-[3-allylamino-2-(p-methoxycinnanoyloxy)propoxy]oxindole
4-[3-allylamino-2-cyclohexylcarbonyloxypropoxy]oxindole and
4-[3-allylamino-2-(1,2-dimethylcyclohexylcarbonyloxy)propoxyl]oxindole.

I claim:
1. A compound of the formula:

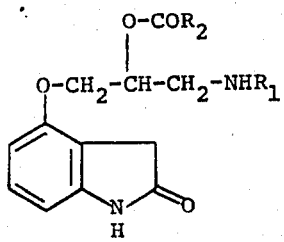

wherein $R_1$ is (i) alkyl of 1 to 4 carbon atoms, (ii) cycloalkyl of 3 to 8 carbon atoms, (iii) phenylalkyl of 8 to 12 carbon atoms in the aggregate thereof, the phenyl ring thereof being separated from the nitrogen atom by at least two carbon atoms, (iv) phenyl alkyl of 8 to 12 carbon atoms in the aggregate thereof, the phenyl ring thereof being separated from the nitrogen atom by at least two carbon atoms and being monosubstituted by alkoxy or alkyl of 1 to 4 carbon atoms, (v) alkenyl or alkinyl of 3 to 7 carbon atoms, or (vi) alkoxycarbonylalkyl, the alkyl moiety having 1 to 6 carbon atoms and the alkoxy moiety having 1 to 4 carbon atoms, and $R_2$ is (i) phenyl, (ii) phenyl monosubstituted by halogen, alkyl of 1 to 4 carbon atoms or alkoxy of 1 to 4 carbon atoms, (iii) phenylalkyl of 7 to 12 carbon atoms in the aggregate thereof or styryl, (iv) phenylalkyl of 7 to 12 carbon atoms in the aggregate thereof or styryl, monosubstituted in the phenyl ring thereof by halogen, alkyl of 1 to 4 carbon atoms or alkoxy of 1 to 4 carbon atoms, (v) pyridyl or thienyl (vi) alkoxycarbonylalkyl, the alkyl moiety having 1 to 6 carbon atoms and the alkoxy moiety having 1 to 4 carbon atoms, (vii) adamantyl, (viii) haloalkyl of 2 to 12 carbon atoms, the halogen thereof being located in other than the α position, or, when $R_1$ is alkenyl of 3 to 7 carbon atoms (ix) alkyl of 1 to 12 carbon atoms, cycloalkyl of 3 to 6 carbon atoms, or cycloalkyl of 3 to 6 carbon atoms mono- or poly-substituted by alkyl of 1 to 4 carbon atoms, furyl or tetrahydropyranyl or a pharmaceutically acceptable acid addition salt thereof.

2. The compound of claim 1, which is 4-[2-(1-adamantylcarbonyloxy)-3-allylaminopropoxy]oxindole.
3. The compound of claim 1, which is 4-(3-tert-butylamino-2-nicotinoyloxypropoxy)oxindole.
4. The compound of claim 1, which is 4-[3-tert-butylamino-2-(2-thenoyloxy)propoxy]oxindole.
5. The compound of claim 1, which is 4-(3-tert-butylamino-2-cinnamoyloxypropoxy)oxindole.
6. The compound of claim 1, which is 4-(2-benzoyloxy-3-tert-butylaminopropoxy)oxindole.
7. The compound of claim 1, which is Malonic acid ethyl-[3-tert-butylamino-1-(2-oxo-4-indolyloxy)-propyl]ester.
8. The compound of claim 1, which is 4-(3-tert-butylamino-2-phenylacetoxypropoxy)oxindole.
9. The compound of claim 1, which is 4-[3-tert-butylamino-2-(4-chlorobutyryloxy)propoxy]oxindole.
10. The compound of claim 1, which is 4-[2-(2-chlorobenzoyloxy)-3-(2-methyl-3-butin-2-ylamino)-propoxy]oxindole.
11. The compound of claim 1, which is 4-[2-(4-methylbenzoyloxy)-3-(2-methyl-4-phenyl-2-butylamino)propoxy]oxindole.
12. The compound of claim 1, which is 2-methyl-2-[2-(3-methoxybenzoyloxy)-3-(2-oxo-4-indolyloxy)-propylamino]propionic acid ethyl ester.
13. The compound of claim 1, which is 4-[3-cyclohexylamino-2-(2-thenoyloxy)propoxy]oxindole.
14. The compound of claim 1, which is 4-(3-allylamino-2-pivaloyloxypropoxy)oxindole.
15. The compound of claim 1, which is 4-[3-allylamino-2-(1-methylcyclohexylcarbonyloxy)-propoxy]oxindole.
16. The compound of claim 1, which is 4-{3-[2-(4-methoxyphenyl)ethylamino]-2-pivaloyloxypropoxy}oxindole.
17. The compound of claim 1, which is 4-[3-(2-methyl-3-buten-2-ylamino)-2-(4-tetrahydropyranylcarbonyloxy)propoxy]oxindole.
18. The compound of claim 1, which is 4-(2-benzoyloxy-3-isopropylaminopropoxy)oxindole.
19. The compound of claim 1, which is 4-[3-(3-pentylamino)-2-(2-thenoyloxy)propoxy]oxindole.
20. A compound of the formula,

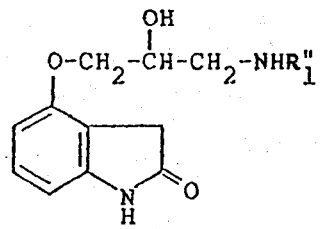

wherein $R_1''$ is alkenyl of 3 to 7 carbon atoms, or a pharmaceutically acceptable acid addition salt thereof.

21. The compound of claim 20, which is 4-(3-allylamino-2-hydroxypropoxy)oxindole.

22. The compound of claim 20, which is 4-[2-hydroxy-3-(2-methyl-3-buten-2-ylamino)propoxy]oxindole.

23. A compound of claim 1, wherein $R_1$ is alkenyl.

24. A compound of claim 1, wherein $R_1$ is branched in the $\alpha$ position.

25. A compound of claim 24, wherein $R_1$ is alkyl.

26. A compound of claim 25, wherein $R_2$ is phenyl, phenyl monosubstituted by halogen of atomic number from 9 to 35, alkyl or alkoxy, pyridyl or thienyl.

27. A compound of claim 26, wherein $R_2$ is phenyl or thienyl.

28. A compound of claim 1, wherein $R_1$ is alkenyl or alkyl, and $R_2$ is phenyl, pyridyl, thienyl, adamantyl, styryl, or haloalkyl, the halogen being of atomic number from 17 to 35.

29. A compound of claim 1, wherein $R_2$ is thienyl or pyridyl or, when R is alkenyl, furyl or tetrahydropyranyl.

30. A compound of the formula:

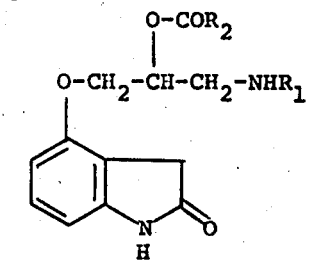

wherein $R_1$ is (i) alkyl of 3 to 5 carbon atoms, (ii) cycloalkyl of 3 to 8 carbon atoms, (iii) phenylalkyl of 8 to 12 carbon atoms in the aggregate thereof, the phenyl ring thereof being separated from the nitrogen atom by at least two carbon atoms, (iv) phenyl alkyl of 8 to 12 carbon atoms in the aggregate thereof, the phenyl ring thereof being separated from the nitrogen atom by at least two carbon atoms and being monsubstituted by alkoxy or alkyl of 1 to 4 carbon atoms, (v) alkenyl or alkinyl of 3 to 7 carbon atoms, or (vi) alkoxycarbonylalkyl, the alkyl moiety having 1 to 6 carbon atoms and the alkoxy moiety having 1 to 4 carbon atoms, and is (i) phenyl, (ii) phenyl monosubstituted by halogen, alkyl of 1 to 4 carbon atoms or alkoxy of 1 to 4 carbon atoms, (iii) phenylalkyl of 7 to 12 carbon atoms in the aggregate thereof or styryl, (iv) phenylalkyl of 7 to 12 carbon atoms in the aggregate thereof or styryl, monosubstituted in the phenyl ring thereof by halogen, alkyl of 1 to 4 carbon atoms or alkoxy of 1 to 4 carbon atoms (v) pyridyl or thienyl (vi) alkoxycarbonylalkyl, the alkyl moiety having 1 to 6 carbon atoms and the alkoxy moiety having 1 to 4 carbon atoms, (vii) adamantyl, (viii) haloalkyl of 2 to 12 carbon atoms, the halogen thereof being located in other than the $\alpha$ position, or, when $R_1$ is alkenyl of 3 to 7 carbon atoms (ix) alkyl of 1 to 12 carbon atoms, cycloalkyl of 3 to 6 carbon atoms, or cycloalkyl of 3 to 6 carbon atoms mono- or poly-substituted by alkyl of 1 to 4 carbon atoms, furyl or tetrahydropyranyl or a pharmaceutically acceptable acid addition salt thereof.

* * * * *